United States Patent [19]

van Leusen et al.

[11] Patent Number: 4,551,278

[45] Date of Patent: Nov. 5, 1985

[54] PREPARATION OF 20-KETO-$\Delta^{16}$-STEROIDS

[75] Inventors: Albert M. van Leusen, Groningen; Adriaan M. van Leusen, Winsum, both of Netherlands

[73] Assignee: Gist-Brocades N.V., Delft, Netherlands

[21] Appl. No.: 604,734

[22] Filed: Apr. 27, 1984

[30] Foreign Application Priority Data

Apr. 29, 1983 [EP] European Pat. Off. ........ 83200617.5

[51] Int. Cl.$^4$ ................................................ C07J 5/00
[52] U.S. Cl. ............................ 260/397.4; 260/397.47; 260/397.3; 260/397.45
[58] Field of Search ............. 260/397.4, 397.45, 397.5, 260/397.47

[56] References Cited

U.S. PATENT DOCUMENTS 3,944,584  3/1976  Chao et al. ................... 260/397.3
4,496,720  1/1985  Bruynes et al. ................ 544/29

Primary Examiner—Elbert L. Roberts
Attorney, Agent, or Firm—Bierman, Peroff & Muserlian

[57] ABSTRACT

A novel process for the preparation of 20-keto-$\Delta^{16}$-steroids comprising reacting a 17-(isocyanosulfonylmethylene)-steroid with an alkylating agent QR$_4$ wherein R$_4$ is an organic group and Q is a group or atom readily displaced with a nucleophile to form a 20-isocyano-20-sulfonyl-$\Delta^{16}$-steroid followed by hydrolysis which are intermediates for the preparation of corticosteroids and the novel intermediates formed therein.

19 Claims, No Drawings

PREPARATION OF 20-KETO-$\Delta^{16}$-STEROIDS

STATE OF THE ART

Steroids are used on a large scale as the active ingredients of many types of pharmaceutical compositions and depending on the substituent pattern of the carbon-skeleton, the steroids can be divided into a number of main classes. An important main class of steroids is formed by the cortico-steroids whose natural representatives are usually produced by the adrenal gland. Corticosteroids are characterized by the presence of a 3-keto group, a $\Delta^4$-double bond, an 11$\beta$-hydroxy group, a 17$\alpha$-hydroxy group and a 17$\beta$-hydroxy-acetyl side chain.

For a long time, corticosteroids were made by chemical degradation of gall acids as cholic acid, desoxycholic acid and glycocholic acid. Afterwards, hecogenin which could be isolated from plants, particularly from numerous Agave species, became an important raw material too. Since the possibility of the introduction of an 11-hydroxy group by microbiological methods, diosenin which could be isolated from numerous Dioscoreacaea species and stigmasterol, usually isolated from the phytosterol mixture from soya or calabar beans, have become the most important raw material for the preparation of corticosteroids.

Much attention has been given to new, cheaper raw materials for the synthesis of pharmaceutically active steroids. Therefore, the degradation of the abundant soya bean derived sterols, sitosterol and campesterol by microbiological methods into 17-oxo-steroids was extensively investigated and as a result thereof, 17-oxo-steroids are readily available now at low prices which makes these compounds, together with the possibility of the introduction of an 11-hydroxy group by microbiological methods, ideal starting materials for corticosteroid synthesis.

A number of chemical synthesis for the construction of the corticosteroid side chain from 17-oxo-steroids is known. For instance, J. Org. Chem., Vol. 44, p. 1582 (1979) describes a method which uses a sulfenate-sulfoxide rearrangement for the introduction of the 17-(dihydroxyacetone) side chain. Another route is described in J.C.S. Chem. Comm., 1981, p. 775 in which the reaction of 17-oxo-steroids with ethyl isocyanoacetate is described followed by a number of other reactions, which ultimately result in the dihydroxyacetone side chain of corticosteroids. Other synthesis of the corticosteroid side chain or of compounds which can be used as precursors therefore are described in J.C.S. Chem. Comm., 1981, p. 774, J.C.S. Chem. Comm., 1982, p. 551, Chem. Ber., Vol. 113, p. 1184 (1980), and J. Org. Chem., 1982 p. 2993.

OBJECTS OF THE INVENTION

It is an object of the invention to provide the novel 17-(20-isocyano-20-sulfonyl)-steroids of formula I and a process for their preparation.

It is another object of the invention to provide a novel process for the preparation of 20-keto-$\Delta^{16}$-steroids.

These and other objects and advantages of the invention will become obvious from the following detailed description.

THE INVENTION

The novel process of the invention for the preparation of 20-keto-$\Delta^{16}$-steroids comprises reacting a 17-(isocyanosulfonylmethylene)-steroid with an alkylating agent QR$_4$ wherein R$_4$ is an organic group and Q is a group or atom readily displaced with a nucleophile to form a 20-isocyano-20-sulfonyl-$\Delta^{16}$-steroid followed by hydrolysis.

In a preferred mode of the process, the starting 17-(isocyanosulfonylmethylene)-steroid has the formula

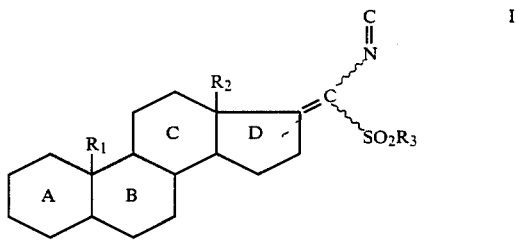

wherein R$_1$ is selected from the group consisting of hydrogen and alkyl of 1 to 4 carbon atoms or may form a double bond in the 1(10), 5(10) or 9(10) position, R$_2$ is selected from the group consisting of hydrogen and alkyl of 1 to 4 carbon atoms, R$_3$ is selected from the group consisting of alkyl of 1 to 10 carbon atoms, dialkylamino of 1 to 8 alkyl carbon atoms, heterocycle of 4 to 8 atoms optionally containing an oxygen atom and aryl optionally substituted with at least one member of the group consisting of halogen and alkyl and alkoxy of 1 to 8 carbon atoms and the A,B,C and D rings may contain at least one double bond and may be optionally substituted with at least one member of the group consisting of hydroxy, amino, oxygen, halogen, alkyl and alkylene and alkoxy of 1 to 6 carbon atoms and alkoxyalkoxy of 2 to 6 carbon atoms and optionally disubstituted with at least one member of the group consisting of epoxy, methylene and alkylenedioxy and alkylenedithio and alkyleneoxythio of 1 to 3 carbon atoms.

The preparation of the compounds of formula I is described in commonly assigned U.S. patent application Ser. No. 604,868 filed on even date herewith entitled "Novel 17-substituted steroids" by reacting a 17-ketosteroid with a sulfonylmethylisocyanide to form the corresponding 17-(formamidosulfonmethylene)-steroid which is dehydrated to form the corresponding isocyanide of formula I.

The process of the invention may be illustrated by the following equation:

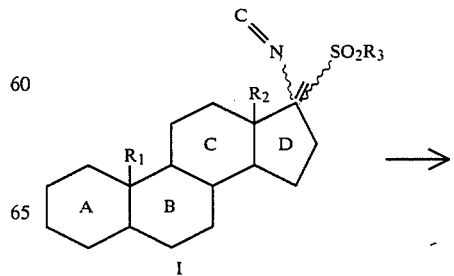

I

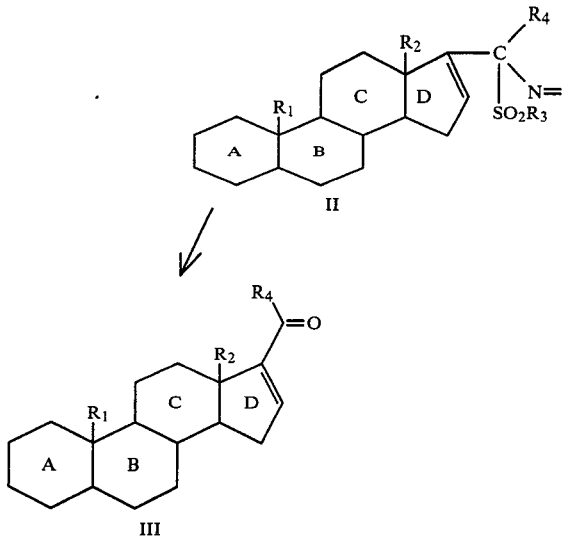

Examples of $R_3$ are alkyl of 1 to 10 carbon atoms such as methyl, ethyl, isopropyl, n-butyl and octyl; dialkylamino with alkyls of 1 to 8 carbon atoms, preferably 1 to 4 carbon atoms, such as dimethylamino or diethylamino; heterocycle of up to 8 ring atoms optionally containing an oxygen ring atom such as pyrriolidine and morpholine; and aryl such as phenyl or naphthyl optionally substituted with at least one member of the group consisting of halogen and alkyl and alkoxy of 1 to 6 carbon atoms such as phenyl, p-methoxyphenyl and p-methylphenyl.

When the rings A,B,C and D contain one or more double bonds, the double bonds are preferably present between $C_1$ and $C_2$, $C_3$ and $C_4$, $C_4$ and $C_5$, $C_5$ and $C_6$, $C_6$ and $C_7$, $C_9$ and $C_{10}$, $C_9$ and $C_{11}$ and/or $C_{11}$ and $C_{12}$. More preferably, the double bond is between $C_4$ and $C_5$ and/or $C_9$ and $C_{11}$. When two or more double bonds are present, the following systems are especially preferred: $C_3(C_4)$ and $C_5(C_6)$, $C_4(C_5)$ and $C_6(C_7)$, $C_1(C_2)$ and $C_4(C_5)$, $C_1(C_2)$, $C_3(C_4)$ and $C_5(C_{10})$ and $C_1(C_2)$, $C_4(C_5)$ and $C_6(C_7)$. Preferably, there is also a double bond between $C_9$ and $C_{11}$.

When the rings A,B,C and D are substituted with hydroxy, suitable substituents are 3-, 9-, 11-, 12- or 14-hydroxy, preferably a 3- or 9-hydroxy. When the rings A,B,C and D are substituted with an amino, suitable aminos are 3-alkylaminos preferably containing 1–4 carbon atoms, 3-dialkylamino groups wherein the alkyls are the same or different and each alkyl preferably contains 1–4 carbon atoms, or amino groups in which the nitrogen atom together with the alkyls form a heterocyclic ring, preferably containing 1–8 ring atoms which ring optionally may contain an oxygen atom. Particularly preferred are dimethylamino, diethylamino, pyrrolidine and morpholine.

When the rings A,B,C and D are substituted with an oxygen atom, the oxygen atom is preferably present at $C_3$, $C_{11}$ or $C_{12}$. When the rings A,B,C and D are substituted with a halogen, suitable halogens are 6-, 9- or 11-florine, chlorine or bromine atoms, preferably 6- or 9-fluorine or chlorine atoms.

When the rings A,B,C and D are substituted by an alkyl, suitable alkyls are 1-, 2-, 6-, 7- or 16-methyl, preferably 1- or 6-methyl. When the rings A,B,C and D are substituted by an alkoxy, suitable alkoxys are 3-, 9-, 11- or 12-alkoxy containing 1–4 carbon atoms, preferably 3-, 9- or 11-methoxy or ethoxy groups. When the rings A,B,C and D are substituted by an alkoxyalkoxy, suitable groups are 3- or 11-methoxymethoxy, methoxyethoxy or tetrahydropyranyloxy. When the rings A,B,C and D are disubstituted, suitable substituents are epoxy groups at $C_1$ and $C_2$ or $C_9$ and $C_{11}$ or a methylene group attached to $C_1$ and $C_2$ or a 3,3-alkylenedioxy, a 3,3-alkylenedithio or a 3,3-alkyleneoxythio group. The alkylene group preferably contains 2 or 3 carbon atoms.

More particularly, the invention relates to compounds in which $R_1$ and $R_2$ are methyl or in which $R_1$ is absent, which are substituted by halogen, especially fluorine or hydroxy at $C_9$ and a hydroxy or keto group at $C_{11}$, or containing functional groups such as a double bond or epoxy group between $C_9$ and $C_{11}$, which can be converted in the art into the groups mentioned before, and which contain a keto group at $C_3$ and double bonds between $C_1$ and $C_2$ and/or $C_4$ and $C_5$, or containing functional groups which can be converted into the keto group and double bonds mentioned above.

The novel process of the invention for the preparation of 20-isocyano-20-sulfonyl-$\Delta^{16}$-steroids comprises reacting a 17-(isocyanosulfonylmethylene)-steroid with an alkylating agent $QR_4$ wherein $R_4$ is an organic group and Q is a group or atom readily displaceable by a nucleophile.

Suitable alkylating agents of the formula $QR_4$ which can be used in the process of the invention are alkylating agents in which $R_4$ is alkyl preferably having 1 to 6 carbon atoms optionally substituted with at least one member of the group consisting of halogen, alkoxy, of 1 to 8 carbon atoms phenylalkoxy, cycloalkyl of 3 to 8 carbon atoms and phenyl optionally substituted with at least one member of the group consisting of halogen, alkyl and alkoxy of 1 to 8 carbon atoms, nitro and cyano. Preferably, $R_4$ is methyl, halomethyl, particularly chloro-, bromo- and iodomethyl, methoxy and benzyloxy. The group Q may be any group which is readily displaced by a nucleophile. Suitable groups are bromine, chlorine, iodine, sulfate, quaternary ammonium and sulfonate.

Preferably the alkylating agent is a methylating agent, especially a methylhalide such as methyliodide. Other preferred alkylating agents are substituted methyl halides wherein the substituent is a halide such as bromine, chlorine and iodine, or an alkoxy group as methoxy or benzyloxy.

The reaction of the 17-(isocyano-sulfonylmethylene)-steroid with the alkylating agent is carried out under basic conditions. Usually the reaction is carried out with a strong alkaline agent in an organic solvent, preferably in an inert gaseous atmosphere. Examples of useful strong alkaline agents are alkali metal alcoholates such as alkali metal t-butylates and alkali metal ethanolates, alkali metal hydrides, alkali metal amides, alkali metal alkyls and alkali metal aryls in which the alkali metal is generally lithium, sodium or potassium. Potassium t-butoxide is preferably used.

The reaction is preferably carried out at lower temperatures, e.g. between $-20°$ and $-80°$ C., preferably between $-30°$ and $-60°$ C., depending on the solvent used too. The reaction is further preferably carried out in a polar organic solvent such as tetrahydrofuran, dimethylformamide, 1,2-dimethoxyethane, hexamethylphosphortriamide, dioxane, benzene, toluene or mixtures thereof. Tetrahydrofuran is preferred. The inert gas atmosphere is preferably a nitrogen or an argon atmosphere.

The reaction can also be carried out in an inert organic solvent to which a base is added. Suitable organic solvents are methylene chloride, chloroform, 1,2-dichloroethane, benzene, toluene, chlorobenzene, dioxane, bis-(2-methoxyethyl)-ether, 1,2-dimethylethane, tetrahydrofuran or mixtures thereof. As the first step and the second step may be performed in a one-pot-reaction, preferably a solvent is used in which the hydrolysis can also be carried out. Suitable bases which can be used are metal hydroxides, and quaternary ammonium and phosphonium hydroxides, preferably alkali metal hydroxide, e.g. potassium hydroxide and quaternary ammonium hydroxides, e.g. triethylbenzylammonium hydroxide. Also alkali metal alcoholates such as potassium-butoxide may be used.

The reaction can be carried out at temperatures between 0° and 100° C., preferably between 0° and 30° C. Sometimes, it may be necessary to add a catalyst to the reaction mixture in the form of an quaternary ammonium or phosphonium salt, for instance trimethylbenzyl ammonium halide, triethylbenzyl ammonium halide, tetrabutyl ammonium halide and alkyl triaryl phosphonium halide. Also crown ethers such as 15-crown-5 or 18-crown-6 can be used.

Furthermore, the reaction can also be performed using phase transfer-conditions, i.e. a two phase system of an organic layer and an aqueous layer to which a phase transfer catalyst has been added. For a general survey of phase transfer reactions see Dhemlov et al, Phase Transfer Catalysis, Weinheim Chemie., 1980.

Suitable organic solvents for the organic layer are methylene chloride, chloroform, 1,2-dichloroethane, benzene, toluene, chlorobenzene and dichlorobenzene. In general, all organic solvents which are immiscible with water and in which the relevant compounds are soluble can be used.

Suitable aqueous layers are solutions of alkali metal hydroxides in water, for example 5 to 50% solutions of lithium hydroxide, sodium hydroxide or potassium hydroxide. Suitable phase transfer catalysts are quaternary ammonium and phosphonium salts and crown-ethers, for instance benzyltrialkyl ammonium halide, tetraalkyl ammonium halides, alkyltriaryl phosphonium halides, 15-crown-5 and 18-crown-6.

The hydrolysis of the 20-isocyano-20-sulfonyl-$\Delta^{16}$-steroids to the 20-keto-$\Delta^{16}$-steroids can be carried out in an organic solvent using an acidic aqueous solution. Suitable organic solvents are, for instance, diethyl ether, methanol and tetrahydrofuran. Suitable acids are dilute strong acids such as hydrogen chloride, sulfuric acid and phosphoric acid. Also acetic acid and formic acid can be used. It is observed that sometimes not only the 20-isocyano-20-sulfonyl group is hydrolyzed, but also other groups linked to the steroid skeleton. These groups may have had the function of protective groups in the preceding reactions.

The invention also relates to the intermediate 20-isocyano-20-sulfonyl-$\Delta^{16}$-steroids of the formula

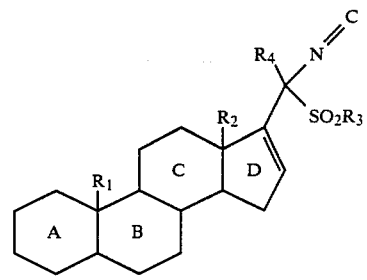

wherein the substituents are as defined above. Furthermore, the invention comprises also the 20-keto-$\Delta^{16}$-steroids as far as these compounds are new.

In the following examples there are described several preferred embodiments to illustrate the invention. However, it should be understood that the invention is not intended to be limited to the specific embodiments. THF is tetrahydrofuran and DME is dimethoxyethane and the specific rotation was measured with light of the sodium D line.

EXAMPLE 1a 3-methoxy-20-isocyano-20-p-methylphenyl-sulfonyl-$\Delta^{3,5,16}$-pregnatriene To a solution of 954 mg (2 mmol 0 of 3-methoxy-17-(isocyano-p-methylphenyl-sulfonylmethylene)-$\Delta^{3,5}$-androstadiene in 40 ml of benzene, 0.3 ml (4.8 mmol) of methyl iodide, 40 mg of benzyltriethylammonium chloride and 20 ml of 50% aqueous NaOH solution were added. The mixture was stirred vigorously for one hour at 80° C. and the decanted organic layer was washed with sodium chloride and dried. After evaporation of the solvent, 910 mg (93% yield) of 3-methoxy-20-isocyano-20-p-methylphenyl-sulfonyl-$\Delta^{3,5,16}$-pregnatriene were obtained melting at 170°–195° C.

IR (Nujol): 2180 (N≡C), 1665, 1640, 1625, 1610 (C═C+Ar), 1345, 1170 (SO$_2$) cm$^{-1}$.

$^1$H NMR (CDCl$_3$): delta 0.7–2.8 (m), 1.0 (s), 2.0 (2×s), 2.49 (s), 3.60 (s, 3H), 5.0–5.4 (m, 2H), 6.20 (m, 1H), 7.32, 7.50, 7.82, 7.98 (ABq, 4H).

EXAMPLE 1b $\Delta^{4,16}$-pregnadiene-3,20-dione 246 mg (0.5 mmol) of the compound of Example 1a were dissolved in 50 ml of diethyl ether and after addition of 20 ml of 15% aqueous HCl solution, the mixture was stirred vigorously at ambient temperature. The organic layer was separated, washed with sodium chloride, washed with saturated NaHCO$_3$ solution and dried over Na$_2$SO$_4$. After evaporation to dryness, 130 mg (70% yield) of $\Delta^{4,6}$-pregnadiene-3,20-dione were obtained melting (after chromatography and sublimation) at 180° C. ($\alpha$)$^{20}$+168° (c 1.0, CHCl$_3$) [Litt. A. Wettstein, Helv. Chim. Act. 27, 1803 (1944); m.p. 186°–188° C., ($\alpha$)$^{21}$+154° (EtOH)].

EXAMPLE 2

3-methoxy-19-nor-$\Delta^{1,3,5(10),16}$-pregnatetraen-20-one 231 mg (0.5 mmol) of 3-methoxy-17-(isocyano-p-methylphenylsulfonylmethylene)-$\Delta^{1,3,5(10)}$-estratriene were dissolved in 3 ml DME. The solution was cooled to −40° C. under a nitrogen atmosphere. After addition of 100 mg (0.8 mmol) of potassium-t-butoxide, 142 mg (0.6 mmol) of methyl iodide were added after 10 minutes. The temperature was slowly raised to +10° C. over two hours and the reaction mixture was added to a mixture of 30 ml of diethyl ether and 2 ml of concentrated aqueous hydrogen chloride solution, followed by vigorously shaking. After filtration of the organic layer over alumina (act. II-III) and evaporation of the solvent, 150 mg (97%) of 3-methoxy-19-nor-$\Delta^{1,3,5(10),16}$-pregnatetraen-20-one were obtained melting at 180° C. Crystallization from ethyl acetate gave the compound with a melting point of 187° C. $(\alpha)^{22}$ +122°.

EXAMPLE 3

3-methoxy-20-isocyano-20-p-methylphenylsulfonyl-21-benzoxy-19-nor-$\Delta^{1,3,5(10),16}$-pregnatetraene 230 mg (0.5 mmol) of 3-methoxy-17-(isocyano-p-methylphenylsulfonylmethylene)-$\Delta^{1,3,5(10)}$-estratriene were dissolved in 3 ml of DME and the solution was cooled under a nitrogen atmosphere to −40° C. 100 mg of potassium-t-butoxide were added followed by 100 mg (0.64 mmol) of chloromethyl benzyl ether after 10 minutes. The temperature was slowly raised over 2.5 hours to +10° C. and the reaction mixture was poured into a saturated solution of NaHCO$_3$ followed by extraction with methylene chloride. The organic layer was dried and evaporated to dryness and the residue was dissolved in methylene chloride. The solution was filtered over alumina (act. II-III) and evaporation of the solvent and crystallization from methanol yielded 105 mg (36%) of 3-methoxy-20-isocyano-20-p-methylphenylsulfonyl-21-benzoxy-19-nor-$\Delta^{1,3,5(10),16}$-pregnatetraene of melting at 153° C. (dec.).

IR (Nujol): 2190 (N≡C), 1620, 1605, 1585 (Ar+C=C), 1330, 1155 (SO$_2$)cm$^{-1}$.

$^1$H NMR (CDCl$_3$): delta 0.75 (s, 3H), 1.1–3.1 (m), 2.38 (s), 3.7 (s, 3H), 3.99 (s, 0.7H), 4.02 (s, 1.3H), 4.53 (s, 2H), 6.25–6.75 (m, 3H), 6.9–7.4 (m, 8H), 7.64, 7.79 (½ ABq, 2H).

Analysis: C$_{36}$H$_{39}$NO$_4$S; molecular weight=581.78. Calculated: %C 74.32, %H 6.76, %N 2.41, %S 5.51. Found: %C 73.8, %H 6.8, %N 2.3, %S 5.4.

The same reaction was also preformed as described in Example 1a but at ambient temperature. Yield after crystallization from methanol was 50%.

The said compound was hydrolyzed as described in Example 1b to obtain 3-methoxy-21-benzoxy-$\Delta^{1,3,5(10),16}$-pregnatetraen-20-one.

EXAMPLE 4

3-methoxy-20-isocyano-20-t-butylsulfonyl-$\Delta^{3,5,16}$-pregnatriene 3-methoxy-20-isocyano-20-t-butylsulfonyl-$\Delta^{3,5,16}$-pregnatriene was obtained in a low yield by the process of Example 1a starting from 3-methoxy-17-(isocyano-t-butylsulfonylmethylene)-$\Delta^{3,5}$-androstadiene.

EXAMPLE 5

3-methoxy-20-isocyano-20-methylsulfonyl-$\Delta^{3,5,16}$-pregnatriene 210 mg of 3-methoxy-20-isocyano-20-methylsulfonyl-$\Delta^{3,5,16}$-pregnatriene were obtained by the process of Example 1a starting from 200 mg of 3-methoxy-17-(isocyanomethylsulfonylmethylene)-$\Delta^{3,5}$-androstadiene.

IR (Nujol): 2180, (N≡C), 1660, 1640 (C=C), 1330, 1160 (SO$_2$).

$^1$H NMR (CDCl$_3$): delta 0.7–2.7 (m), 1.0 (s), 1.10 (s), 1.97 (s), 2.00 (s), 3.02 (s, 3H), 3.55 (s, 3H), 5.0–5.4 (m, 2H), 6.1–6.3 (m), 6.4–6.6 (m).

Hydrolysis of the said compound gave a 35% yield of $\Delta^{4,6}$-pregnadiene-3,20-dione.

EXAMPLE 6

3-methoxy-20-isocyano-20-n-decylsulfonyl-$\Delta^{3,5,16}$-pregnatriene 3-methoxy-20-isocyano-20-n-decylsulfonyl-$\Delta^{3,5,16}$-pregnatriene was prepared by the method of Example 1a starting from 527 mg of 3-methoxy-17-(isocyano-20-n-decylsulfonylmethylene)-$\Delta^{3,5}$-androstadiene.

IR (Neat): 2160 (N≡C), 1655, 1630 (C=C).

$^1$H NMR (CDCl$_3$): delta 0.6–3.5 (m), 1.0 (s), 1.11, (s), 1.3 (s, br), 1.98 (s, br), 3.56 (s, 3H), 5.0–5.3 (m, 2H), 6.05–6.25 (m), 6.3–6.5 (m).

Hydrolysis of the said compound gave a 45% yield of $\Delta^{4,6}$-pregnadiene-3,20-dione.

EXAMPLE 7

3-methoxy-20-isocyano-p-methoxyphenylsulfonyl-$\Delta^{3,5,16}$-pregnatriene

A 92% yield of 3-methoxy-20-isocyano-p-methoxyphenylsulfonyl-$\Delta^{3,5,16}$-pregnatriene melting at 160°–180° C. (dec.) was prepared by the method of Example 1a starting from 3-methoxy-17-(isocyano-20-p-methoxyphenylsulfonylmethylene)-$\Delta^{3,5}$-androstadiene using toluene instead of benzene.

IR (Nujol): 2160 (N≡C), 1660, 1635, 1600, 1585 (C=C), 1335, 1150 (SO$_2$).

$^1$H (CDCl$_3$): delta 0.74–2.77 (m), 0.94 (s),1.92) (s), 3.55 (s, 3H), 3,88(8s, 3H), 5.04–5.35 (m, 2H), 6.13 (m, 1H), 6.95, 7.09, 7.78, 7.93 (ABq. 4H).

Hydrolysis of the said compound gave a 57% yield of $\Delta^{4,16}$-pregnadiene-3,20-dione.

Various modifications of the products and process of the invention may be made without departing from the spirit or scope thereof and it should be understood that the invention is intended to be limited only as defined in the appended claims.

EXAMPLE 8a 3-methoxy-20-isocyano-20-p-methylphenylsulfonyl-21-benzoxy-pregna-3,5,16-diene The title compound was prepared according to the process described in Example 1a starting from 3-methoxy-17-(isocyano-p-methylphenylsulfonylmethylene)-androsta-3,5-diene (954 mg, 2 mmol) and chloromethyl benzylether (470 mg, 3 mmol). The product obtained was purified by filtration over alumina (act. 2-3). Crystallization from methanol at −20° C. gave 645 mg (54%) of the title compound, m.p. 90°–115° C. (dec.).

IR (Nujol): 2150 (N≡C), 1650, 1625, 1590 (C=C), 1325, 1140 (SO$_2$), 1090 (C—O—C).

$^1$H NMR (CDCl$_3$): delta 0.67–2.77 (m), 0.76 (s), 0.98 (s), 2.37 (s), 3.53 (s, 3H), 3.77, 3.94, 4.02, 4.19 (q, 2H), 5.54 (s, 2H), 5.03–5.30 (m, 2H), 6.29–6.47 (m, 1H), 6.98–7.47 (m, 7H), 7.76, 7.83 (½AB, 2H).

EXAMPLE 8b 21-benzoxy-pregna-4,16-diene-3,20-dione

The compound prepared in Example 8a (448 mg) was hydrolized in methylenechloride (15 ml) and diethylether (45 ml) at 0° C. for half an hour. Yield: 210 mg containing 75% of the title compound.

IR (Nujol): 1670 (C=O), 1620, 1590 (C=C), 1110 (C—O—C).

$^1$H NMR (CDCl$_3$): delta 0.70–2.90 (m), 0.97 (s), 1.22 (s), 4.33 (s, 2H), 4.57 (s, 2H), 5.70 (s, 1H), 6.62–6.82 (m, 1H), 7.19 (s, 5H).

EXAMPLE 9a 20-isocyano-20-p-methylphenylsulfonyl-pregna-1,4,16-triene-3-one

The title compound was prepared according to the process described in Example 1a starting from 17-isocyano-p-methylphenylsulfonylmethylene)-androsta-1,4-diene-3-one (462 mg, 1 mmol). Yield 450 mg (95%, m.p. 160°–175° C. (dec.).

IR (Nujol): 2140 (N=C), 1660 (C=O), 1620, 1595 (C=C), 1325, 1150 (SO$_2$).

$^1$H NMR (CDCl$_3$): delta 0.70–3.27 (m), 0.92 (s), 1.01 (s), 1.23 (s), 1.91 (s), 2.42 (s), 6.05, 6.08, 6.26, 6.29 (2×d, 2H), 6.92, 7.09 (d, 1H), 7.28, 7.40, 7.73, 7.86 (AB, 4H).

EXAMPLE 9b pregna-1,4,16-triene-3,20-dione

The compound prepared in Example 9a (450 mg) was hydrolized in methylenechloride (15 ml) and diethylether (30 ml) at 20° C. for two minutes. The product obtained was purified by filtration over alumina. Yield 235 mg (75%). Crystallization from methanol gave the title product, m.p. 200°–204° C. (dec.) (alpha)$^{22}$+134 (CHCl$_3$, c 1.00).

IR (Nujol): 1680 (C=O), 1630, 1610, 1590 C=C).

$^1$H NMR (CDCl$_3$): delta 0.53–2.86 (m), 0.98 (s), 1.29 (s), 2.27 (s), 6.04, 6.07, 6.24, 6.27 (2×d, 2H), 6.55–6.77 (m, 1H), 6.95–7.11 (d, 1H).

EXAMPLE 10a 3-methoxy-20-isocyano-p-methylphenylsulfonylpregna-3,5,9(11),16-tetra-ene The title compound was prepared according to the process described in Example 8a starting from 3-methoxy-17-(isocyano-p-methylphenylsulfonylmethylene)-androsta-3,5,9(11)-triene (476 mg, 1 mmol). Yield: 460 mg (94%).

IR (Nujol): 2140 (N=C), 1655, 1630, 1595 (C=C), 1320, 1150 cm$^{-1}$ (SO$_2$).

$^1$H NMR (CDCl$_3$): delta 0.60–2.88 (m), 0.73 (s), 0.96 (s) 1.17 (s), 1.98 (s), 2.48 (s), 3.58 (s, 3H), 5.07–5.63 (m, 3H), 6.09–6.39 (m, 1H), 7.27, 7.41, 7.76, 7.90 (AB, 4H).

EXAMPLE 10b

Pregna-4,9(11),16-triene-3,20-dione

The title compound was prepared by hydrolysis of the compound prepared in Example 10a (245 mg, 0.5 mmol) in a mixture of methylenechloride (10 ml) and diethyl ether (40 ml). The reaction mixture was stirred with hydrochloric acid (20 ml) at 0° C. for 1.5 hours. Yield: 125 mg containing 75% of the title compound, m.p. 190°–195° C., after two crystallizations from methanol. (alpha)$^{20}$+225 (CHCl$_3$, c 1.00).

IR (Nujol): 1665 (C=O), 1620, 1595 (C=C).

$^1$H NMR (CDCl$_3$): delta 0.75–3.12 (m), 0.90 (s), 1.39 (s), 2.31 (s), 5.42–5.68 (m, 1H), 5.77 (s, 1H), 6.63–6.87 (m, 1H).

EXAMPLE 11a 20-isocyano-20-p-methylphenylsulfonyl-21-benzoxy-pregna-1,4,16-triene-3-one The title compound was prepared according to the method described in Example 8a, starting from 17-(isocyano-p-methylphenylsulfonylmethylene)-androsta-1,4-diene-3-one (462 mg, 1 mmol). Yield: 625 mg of a mixture of the title compound and chloromethyl benzylether (1:1).

$^1$H NMR (CDCl$_3$): delta 0.57–3.00 (m), 0.80 (s), 1.01 (s), 1.19 (s), 2.38 (s), 3.69–4.26 (m, 2H), 4.53 (s, 2H), 5.92–6.51 (m, 3H), 6.80–7.51 (m, 8H), 7.70–7.84 (AB, 2H).

EXAMPLE 11b 21-benzoxy-pregna-1,4,16-triene-3,20-dione

The title compound was prepared according to the method described in Example 9b starting from the reaction mixture of Example 11a. Crystallization from methanol (−20° C.) afforded 195 mg (47%) of the title compound, m.p. 193°–198° C. (dec.).

IR (Nujol): 1660 (C=O), 1625, 1605, 1585 (C=C), 1110 (C—O—C).

$^1$H NMR (CDCl$_3$): delta 0.62–2.93 (m), 1.00 (s), 1.27 (s), 4.35 (s, 2H), 4.59 (s, 2H), 6.05, 6.09, 6.27, 6.31 (2×d, 2H), 6.62–6.79 (m, 1H), 6.95, 7.12 (d, 1H), 7.28 (s, 5H).

EXAMPLE 12a 3-methoxy-20-isocyano-20-p-methylphenylsulfonyl-21-chloropregna-3,5,9(11),16-tetra-ene 3-Methoxy-17-(isocyano-p-methylphenylsulfonylmethylene)-androsta-3,5,9(11)-triene (476 mg, 1.00 mmol) and triethylbenzylammonium chloride (20 mg) were dissolved in methylene chloride (10 ml). After stirring for 2 hours at 25° C. with a sodium hydroxide solution (5 ml, 50%), the organic layer was seperated and dried over Na$_2$SO$_4$, followed by filtration over alumina (act. II–III). Evaporation of the solvent afforded the title compound (368 mg, 70%).

IR (Nujol): 1150 (N=C), 1660, 1635, 1600 (C=C), 1340, 1155 (SO$_2$).

$^1$H NMR (CDCl$_3$): delta 0.44–2.90 (m), 0.57 (s), 0.98 (s), 1.13 (s), 3.56 (s, 3H), 3.79–4.35 (s+m, 2H), 5.05–5.62 (m, 3H), 6.08–6.60 (m, 1H), 7.29, 7.44, 7.77, 7.92 (AB, 4H).

EXAMPLE 12b 21-chloro-pregna-4,9(11),16-triene-3,20-dione

The title compound was prepared to the process described in Example 10b, starting with the reaction mixture of Example 12a. Yield: 145 mg of a mixture containing 65% of the title compound.

IR (Nujol): 1670 (C=O), 1620, 1595 (C=C).

$^1$H NMR (CDCl$_3$): delta 0.62–3.09 (m), 0.90 (s), 1.36 (s), 4.38 (s, 2H), 5.22–5.88 (m, 2H), 6.74–6.92 (m, 1H).

EXAMPLE 13a 3-methoxy-20-isocyano-20-p-methylphenylsulfonyl-21-methylpregna-3,5,16-triene The title compound was prepared according to the method described in Example 8a starting from 3-methoxy-17-(isocyano-p-methylphenylsulfonylmethylene)-androsta-3,5-diene (954 mg, 2 mmol) and ethyl iodide (4.9 mmol). Yield: 900 mg (89%), m.p. 135°–150° C.

IR (Nujol): 2170 (N≡C), 1660, 1635, 1605 (C=C), 1340, 1160, (SO₂).

¹H NMR (CDCl₃): delta 0.45–2.74 (m), 0.60 (s), 0.97 (s), 2.46 (s), 3.47 (s, 3H), 4.88–5.27 (m, 2H), 5.82–6.01, 6.20–6.39 (2×m, 1H), 7.08, 7.24, 7.58, 7.74 (AB, 4H).

EXAMPLE 13b

21-methyl-pregna-4,16-diene-3,20-dione

The title compound was prepared by hydrolysis of the compound prepared in Example 13a (253 mg, 0.5 mmol) according to the process described in Example 10b. Yield: 140 mg of a mixture containing 75% of the product.

IR (Nujol): 1665 (C=O), 1615, 1590 (C=C).

¹H NMR (CDCl₃): delta 0.50–3.05 (m), 1.00 (s), 1.12 (t), 5.66 (s, 1H), 6.50–6.74 (m, 1H).

EXAMPLE 14a

3-methoxy-20-isocyano-20-p-methylphenylsulfonyl-21-chloro-19-nor-pregna-1,3,5(10),16-tetraene The title compound was prepared according to the process described in Example 12, starting with 3-methoxy-17-(isocyano-p-methylphenylsulfonylmethylene)-estra-1,3,5(10)-triene (461 mg, 1 mmol). Yield: 510 mg.

IR (Nujol): 2160 (N≡C).

¹H NMR (CDCl₃): delta 0.6–3.2 (m), 0.65 (s), 1.01 (s), 1.51 (s), 2.48 (s), 3.77 (s, 3H), 3.9–4.2 (m, 2H), 6.05–6.25 (m, 0.5H), 6.45–6.85 (m, 0.5H), 7.0–7.6 (m), 7.81, 7.94 (½AB, 2H).

EXAMPLE 14b

3-methoxy-21-chloro-19-nor-pregna-1,3,5(10),16-tetraen-20-one

The title compound was prepared by hydrolysis of the reaction mixture of Example 14a (510 mg) in a mixture of methylene chloride (7.5 ml) and diethylether (20 ml). The reaction mixture was stirred with hydrochloric acid (10 ml, 36%) at 20° C. for 10 minutes. Chromatography (diethylether, alumina act. II–III) afforded 100 mg of the title compound (29%), m.p. 134°–141° C. (from diethylether).

IR (Nujol): 1680 (C=O).

¹H NMR (CDCl₃): delta 0.75–3.25 (m), 0.92 (s), 3.72 (s, 3H), 4.33 (s, 2H), 6.5–6.9 (m, 3H), 7.0–7.3 (m, 1H). Exact mass 344.154 (calcd. 344.153).

EXAMPLE 15a

3-methoxy-20-isocyano-20-p-methylphenylsulfonyl-21-chloro-pregna-3,5,16-triene The title compound was prepared according to Example 12a starting with 3-methoxy-17-isocyano-p-methylphenylsulfonylmethylene)-androsta-3,5-diene (477 mg, 1 mmol). Yield: 470 mg.

IR (Nujol): 2160 (N≡C), 1655, 1630, 1595 (C=C), 1340–1155 (SO₂).

¹H NMR (CDCl₃): delta 0.5–2.7 (m), 0.65 (s), 0.95 (s), 1.02 (s), 2.45 (s), 3.52 (s, 3H), 3.75–4.35 (m, 2H), 5.0–5.35 (m, 2H), 6.0–6.25 (m, 0.4H), 6.3–6.6 (m, 0.6H), 7.29, 7.42, 7.74, 7.88 (AB, 4H).

EXAMPLE 15b

21-chloro-pregna-4,16-diene-3,20-dione

The title compound was prepared by hydrolysis of the compound prepared in Example 15a in a mixture of methylene chloride (5 ml) and diethyl ether (25 ml). This mixture was stirred vigorously with hydrochloric acid (2 ml, 38%), for 5 minutes. After work up and chromatography (methylene chloride, alumina act. II–III) the title compound was obtained (55 mg, 15%).

IR (Nujol): 1675 (C=O).

¹H NMR (CDCl₃): delta 0.7–2.7 (m), 0.89 (s), 1.21 (s), 4.34 (s, 2H, 5.73 (s, 1H), 6.65–6.90 (m, 1H), Exact mass: 346.169 (calcd. 346.170).

EXAMPLE 16

3-methoxy-20-isocyano-20-p-methylphenylsulfonyl-21-bromo-19-nor-pregna-1,3,5(10),16-tetraene The title compound was prepared according to the process described in Example 12a, starting with 3-methoxy-17-(isocyano-p-methylphenylsulfonylmethylene)-estra-1,3,5(10)-triene (461 mg, 1 mmol) in a solution of dibromomethane (5 ml). Yield: 475 mg.

IR (Nujol): 2160 (N≡C), 1340, 1160 (SO₂).

¹H NMR (CDCl₃): delta 0.6–3.2 (m), 0.69 (s), 0.97 (s), 1.07 (s), 2.46 (s), 3.7–4.2 (m, 5H), 3.73 (s), 3.90 (s), 6.05–6.25 (m, 0.2H), 6.4–6.9 (m, 2.2H), 7.08 (s, 1H), 7.28, 7.42, 7.79, 7.93 (AB, 4H).

EXAMPLE 17a

3-methoxy-20-isocyano-p-methylphenylsulfonyl-21-bromo-pregna-3,5,16-triene

The title compound was prepared according to the process described in Example 12a, starting with 3-methoxy-17-(isocyano-p-methylphenylsulfonylmethylene)-androsta-3,5-diene (477 mg, 1 mmol). Methanol (20 ml) was added to the crude product and vibrated in an ultrasonic bath. The solid was sucked off and dried (product A, 247 mg). The mother liquid was evaporated yielding a second product (B, 190 mg). According to NMR the products appeared to be two stereoisomers of the title compound.

IR (Nujol): 2150 (N≡C), 1655, 1630, 1600 (C=C), 1335, 1150 (SO₂).

¹H NMR (CDCl₃): product A, delta 0.5–2.7 (m), 0.65 (s), 0.95 (s), 2.44 (s), 3.51 (s, 3H), 3.86 (s, 2H), 5.0–5.35 (m, 2H), 6.3–6.6 (m, 1H), 7.27, 7.41, 7.73, 7.88 (ABq, 4H).

¹H NMR (CDCl₃): product B, delta 0.5–2.7 (m), 0.97 (s), 1.04 (s), 2.43 (s), 3.4–4.5 (m, 5H), 3.52 (s), 3.68 (s), 3.80 (s), 3.98 (s), 4.13 (s), 4.40 (s), 5.0–5.35 (m, 2H), 9–6.2 (m, 1H), 7.29, 7.43, 7.73, 7.88 (ABq, 4H).

EXAMPLE 17b

21-bromo-pregna-4,16-diene-3,20-dione

The title product was obtained by hydrolysis of the product prepared in Example 17a. The hydrolysis was carried out with hydrobromic acid (6 ml, 48%) at 0° C. during 1.5 hours. The reaction mixture was neutralized with NaHCO₃ and extracted with methylenechloride. After drying and evaporation in vacuo an oil was obtained. Chromatography over alumina with methylene chloride afforded 90 mg of the title compound (23%), m.p. 141–143 (from diethylether).

IR (Nujol): 1660 (C=O).

¹H NMR (CDCl₃): delta 0.7–2.7 (m), 0.98 (s), 1.21 (s), 4.10 (s, 2H), 5.73 (s, 1H), 6.65–6.90 (m, 1H).

EXAMPLE 18a 3-methoxy-20-isocyano-20-p-methylphenylsulfonyl-21-methoxypregna-3,5,16-triene The title compound was prepared according to the process described in Example 8a, starting with 3-methoxy-17-(isocyano-p-methylphenylsulfonylmethylene)-androsta-3,5-diene (477 mg, 1 mmol) and chloromethylmethylether (0.2 ml). Yield: 385 mg.

IR (Nujol): 2160 (N≡C).

$^1$H NMR (CDCl$_3$): delta 0.5–3.0 (m), 0.79 (s), 1.00 (s), 1.04 (s), 2.45 (s), 3.39 (s, 3H), 3.56 (s, 3H), 3.95 (s, 2H), 5.05–5.40 (m, 2H), 6.05–6.30 (m, 0.3H), 6.35–6.60 (m, 0.7H), 7.30, 7.45, 7.80, 7.95 (AB, 4H).

EXAMPLE 18b 21-methoxy-pregna-4,16-diene-3,20-dione

The organic phase of the reaction mixture of Example 18a was hydrolized with hydrochloric acid (7.5 ml, 25%). Chromatography over alumina (act. II–III) with methylene chloride afforded the title compound (130 mg, 38%).

IR (Nujol): 1685 (sh), 1665 (C=O), 1615 C=C).

$^1$H NMR (CDCl$_3$): delta 0.6–2.8 (m), 0.97 (s), 1.21 (s), 3.40 (s, 3H), 4.28 (s, 2H), 5.72 (s, 1H), 6.65–6.85 (m, 1H). Exact mass 342.218 (calcd. 342.219).

EXAMPLE 19a 3-methoxy-20-isocyano-20-p-methylphenylsulfonyl-21-methoxy-19-nor-pregna-1,3,5(10),16-tetraene The title compound was prepared according to the process described in Example 8a, starting with 3-methoxy-17-(isocyano-p-methylphenylsulfonylmethylene)-estra-1,3,5(10)-triene (461 mg, 1 mmol) and chloromethylether. Yield 355 mg brown oil.

$^1$H NMR (CDCl$_3$): delta 0.6–3.1 (m, 0.73 (s), 0.97 (s), 2.42 (s), 3.35, 3.38, 2×s, 3H), 3.70 (s, 3H), 3.97 (s, 2H), 6.0–6.9 (m, 3H), 7.0–7.5 (m, 2H), 7.80, 7.93 (½AB, 2H).

EXAMPLE 19b 3,21-dimethoxy-19-nor-pregna-1,3,5(10),16-tetraene-20-one

The reaction product of Example 19a was dissolved in diethylether (40 ml) and methylene cloride (5 ml) and vigorously stirred with hydrochloric acid (5 ml, 38%). After work up and chromatography over alumina (act. II–III) with dichloromethane the title compound was obtained (50 mg, 15%), m.p. 95°–100° C. (from diethyl ether).

IR (Nujol): 1675 (C=O).

$^1$H NMR (CDCL$_3$): delta 0.8–3.2 (m), 0.95 (s), 3.42 (s, 3H), 3.75 (s, 3H), 4.30 (s, 2H), 6.5–6.9 (m, 3H), 7.13 (s, 1H). Exact mass 340.204 (calcd. 340.204).

What we claim is:

1. A process for the preparation of 20-keto-Δ$^{16}$-steroids comprising reacting a 17-(isocyanosulfonylmethylene)-steroid with an alkylating agent QR$_4$ wherein R$_4$ is an organic group and Q is a group or atom readily displaced with a nucleophile to form a 20-isocyano-20-sulfonyl-Δ$^{16}$-steroid followed by hydrolysis.

2. A process for the preparation of 20-isocyano-20-sulfonyl-Δ$^{16}$-steroids comprising reacting a 17-(isocyanosulfonylmethylene)-steroid with an alkylating agent QR$_4$ wherein R$_4$ is an organic group and Q is a group or atom easily displaced by an nucleophile.

3. The process of claim 1 or 2 wherein the reaction with the isocyano compound and the alkylating agent is effected under basic conditions.

4. The process of claim 3 wherein the base is selected from the group consisting of alkali metal hydroxide, alkali metal alcoholate, phosphonium hydroxides and a quaternary ammonium hydroxide and the reaction is effected in an inert organic solvent 5. The process of claim 1 or 2 wherein a catalyst selected from the group consisting of quaternary ammonium salts, phosphonium salts and a crown ether is present.

6. The process of claim 1 wherein the reaction is effected under phase-transfer conditions.

7. The process of claim 1 or 2 wherein Q is selected from the group consisting of bromine, chlorine, iodine, quaternary ammonium and sulfonate.

8. The process of claim 1 or 2 wherein R$_4$ is selected from the group consisting of alkyl of 1 to 6 carbon atoms optionally substituted with at least one halogen, alkoxy of 1 to 8 carbon atoms, phenylalkyl of 1 to 8 carbon atoms, cycloalkyl of 3 to 8 carbon atoms and phenyl optionally substituted with at least one member of the group consisting of halogen, alkyl and alkoxy of 1 to 8 carbon atoms, —NO$_2$ and —CN.

9. The process of claim 8 wherein R$_4$ is selected from the group consisting of methyl, chloromethyl, iodomethyl, bromomethyl and benzyloxy.

10. The process of claim 1 wherein the hydrolysis is effected in an organic solvent with an aqueous acid.

11. The process of claim 1 wherein the starting 17-(isocyanosulfonylmethylene)-steroid has the formula

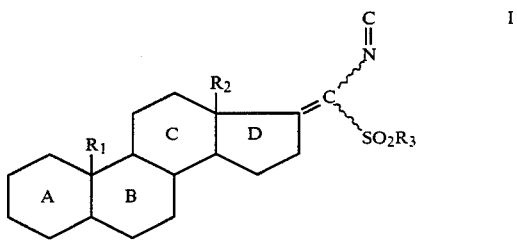

wherein R$_1$ is selected from the group consisting of hydrogen and alkyl of 1 to 4 carbon atoms or may form a double bond in the 1(10), 5(10) or 9(10) position, R$_2$ is selected from the group consisting of hydrogen and alkyl of 1 to 4 carbon atoms, R$_3$ is selected from the group consisting of alkyl of 1 to 10 carbon atoms, dialkylamino of 1 to 8 alkyl carbon atoms, heterocycle of 4 to 8 atoms optionally containing an oxygen atom and aryl optionally substituted with at least one member of the group consisting of halogen and alkyl and alkoxy of 1 to 8 carbon atoms and the A,B,C and D rings may contain at least one double bond and may be optionally substituted with at least one member of the group consisting of hydroxy, amino, oxygen, halogen, alkyl and alkylene and alkoxy of 1 to 6 carbon atoms and alkoxyalkoxy of 2 to 6 carbon atoms and optionally disubstituted with at least one member of the group consisting of epoxy, methylene and alkylenedioxy and alkylenedithio and alkyleneoxythio of 1 to 3 carbon atoms.

12. The process of claim 11 wherein R$_3$ is selected from the group consisting of alkyl of 1 to 10 carbon atoms and phenyl and naphthyl optionally substituted with at least one member of the group consisting of halogen, alkyl of 1 to 6 carbon atoms and alkoxy of 1 to 6 carbon atoms.

13. The process of claim 11 wherein $R_3$ is selected from the group consisting of phenyl, p-methoxyphenyl and p-methylphenyl.

14. The process of claim 11 having a steroid with at least one double bond selected from the group consisting of 1(2), 3(4), 4(5), 5(6), 6(7), 9(11) and 11(12).

15. The process of claim 11 having a steroid with at least one substituent selected from the group consisting of hydroxy at 3-, 9-, 11-, 12- and 14-positions, keto at 3-, 11- and 12-positions, fluorine, chlorine and bromine in the 6-, 9- and 11-positions, methyl in the 1- and 6-positions, alkoxy of 1 to 4 carbon atoms in the 3-, 9- and 11-positions and alkoxyalkoxy of 2 to 6 carbon atoms in the 3- and 11-positions.

16. The process of claim 11 having a steroid with at least one substituent selected from the group consisting of 1,2-epoxy, 9,11-epoxy, 1,2-methylene, and 3,3-alkylenedioxy, 3,3-alkylenedithio and 3,3-alkyleneoxythio of 1 to 4 alkylene carbon atoms.

17. A compound of the formula

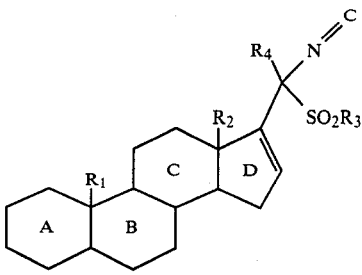

wherein $R_1$ is selected from the group consisting of hydrogen and alkyl of 1 to 4 carbon atoms or may form a double bond in the 1(10), 5(10) or 9(10) position, $R_2$ is selected from the group consisting of hydrogen and alkyl of 1 to 4 carbon atoms, $R_3$ is selected from the group consisting of alkyl of 1 to 10 carbon atoms, dialkylamino of 1 to 8 alkyl carbon atoms, heterocycle of 4 to 8 atoms optionally containing an oxygen atom and aryl optionally substituted with at least one member of the group consisting of halogen and alkyl and alkoxy of 1 to 8 carbon atoms and the A,B,C and D rings may contain at least one double bond and may be optionally substituted with at least one member of the group consisting of hydroxy, amino, oxygen, halogen, alkyl and alkylene and alkoxy of 1 to 6 carbon atoms and alkoxyalkoxy of 2 to 6 carbon atoms and optionally disubstituted with at least one member of the group consisting of epoxy, methylene and alkylenedioxy and alkylenedithio and alkyleneoxythio of 1 to 3 carbon atoms and $R_4$ is an organic group.

18. A process for the preparation of a 20-keto-$\Delta^{16}$-steroid comprising hydrolyzing a 20-isocyano-20-sulfonyl-$\Delta^{16}$-steroid.

19. The process of claim 8 wherein the starting compound is a compound of claim 17.

* * * * *